(12) United States Patent
Coppens

(10) Patent No.: US 7,484,253 B1
(45) Date of Patent: Feb. 3, 2009

(54) PATIENT SUPPORT ELEMENT FOR RADIATION THERAPY THAT REDUCES SKIN RADIATION BURN

(75) Inventor: Daniel D. Coppens, Avondale, PA (US)

(73) Assignee: Qfix Systems, LLC, Avondale, PA (US)

(*) Notice: Subject to any disclaimer, the term of this patent is extended or adjusted under 35 U.S.C. 154(b) by 381 days.

(21) Appl. No.: 10/852,413

(22) Filed: May 23, 2004

Related U.S. Application Data

(60) Provisional application No. 60/473,584, filed on May 27, 2003.

(51) Int. Cl.
*A61G 13/00* (2006.01)
*A61G 13/12* (2006.01)

(52) U.S. Cl. .......................... 5/601; 378/209; 600/415

(58) Field of Classification Search .............. 5/601, 5/600; 378/209, 208; 600/415
See application file for complete search history.

(56) References Cited

U.S. PATENT DOCUMENTS

| | | | |
|---|---|---|---|
| 3,947,686 A | 3/1976 | Cooper et al. | |
| 4,145,612 A | 3/1979 | Cooper et al. | |
| 4,312,912 A | 1/1982 | Tamura et al. | |
| 5,537,454 A | 7/1996 | Korver, II et al. | |
| 5,771,513 A | 6/1998 | Kirchgeorg et al. | |
| 7,082,631 B2* | 8/2006 | Czop ............................. | 5/484 |
| 2006/0185087 A1 | 8/2006 | Coppens et al. | |

FOREIGN PATENT DOCUMENTS

| | | |
|---|---|---|
| GB | 1 435 223 A | 5/1976 |
| WO | WO 94/08542 A | 4/1994 |

* cited by examiner

*Primary Examiner*—Alexander Grosz
(74) *Attorney, Agent, or Firm*—Gomez International Patent Office, LLC

(57) ABSTRACT

A multi-layer patient support element comprising at least one structural member, wherein the structural member has a top surface and a bottom surface and wherein the top surface comprises a low radiation absorbing separation member. The support element of the present invention can be integrated into a patient support surface, used as an insert or easily removable from the patient support surface. The support element can reduce or eliminate radiation skin burn caused during radiation therapy.

17 Claims, 6 Drawing Sheets

PATIENT SUPPORT ELEMENT FOR RADIATION THERAPY THAT REDUCES SKIN RADIATION BURN

CROSS-REFERENCE TO RELATED APPLICATIONS

This application is based on provisional application 60/473,584 filed May 27, 2003.

BACKGROUND OF THE INVENTION

Traditional patient support devices used in radiation therapy often use an open cross-weave of polymer monofilaments strung taught in the same manner as a tennis racquet. This generally performs well from the standpoint of patient surface dosage but is impractical for many patient support surfaces and devices. In addition, it does not provide the precise positioning required for state of the art treatment techniques. Diagnostic imaging table technology has been used successfully in radiation therapy to a certain extent. However, the dosage that occurs at the contact point between the patient and support surface can be high. This high dosage can cause radiation burns on the patient's skin.

Diagnostic imaging tables are generally manufactured from carbon fiber skins on a foam core. Skin burn occurs because the relatively thick carbon fiber layer results in electron generation by Compton scattering. Some of this electron energy is directed at the patient. Electrons travel a relatively short distance. When the patient is in intimate contact with the scattering surface, a large dose of electron energy may be deposited in the patients skin, causing serious skin burn. Therefore, there is a need for a patient support element that can reduce or eliminate radiation skin burn yet provide precise positioning of a patient.

SUMMARY OF THE INVENTION

The present invention solves the above-mentioned problems by separating the patient's skin from the structural element, thereby significantly decreasing the patient radiation skin dosage caused by electron scatter. Specifically, the present invention provides a multi-layer patient support element comprising at least one structural member, wherein the structural member has a top surface and a bottom surface and wherein the top surface comprises a low radiation absorbing separation member.

DETAILED DESCRIPTION OF THE INVENTION

Modern radiation therapy techniques, such as Inter-Modulated Radiation Therapy (IMRT), require precise and repeatable patient location, positioning and immobilization. For this reason, it is insufficient to simply place a cushion or pad between the patient and device/tabletop. The present invention provides an additional thin, rigid and low radiation-absorbing surface placed between the patient and structural element. This separation member separates the patient from the device by a thin layer of very low radiation absorbing materials such as rigid foam. This creates a low scatter surface next to the patient's skin and maintains the required rigidity needed in modern radiation therapy. For example, when employed in a patient support table, the separation member provides a rigid reference surface that can be used to accurately and repeatedly position the patient.

Figure 1:
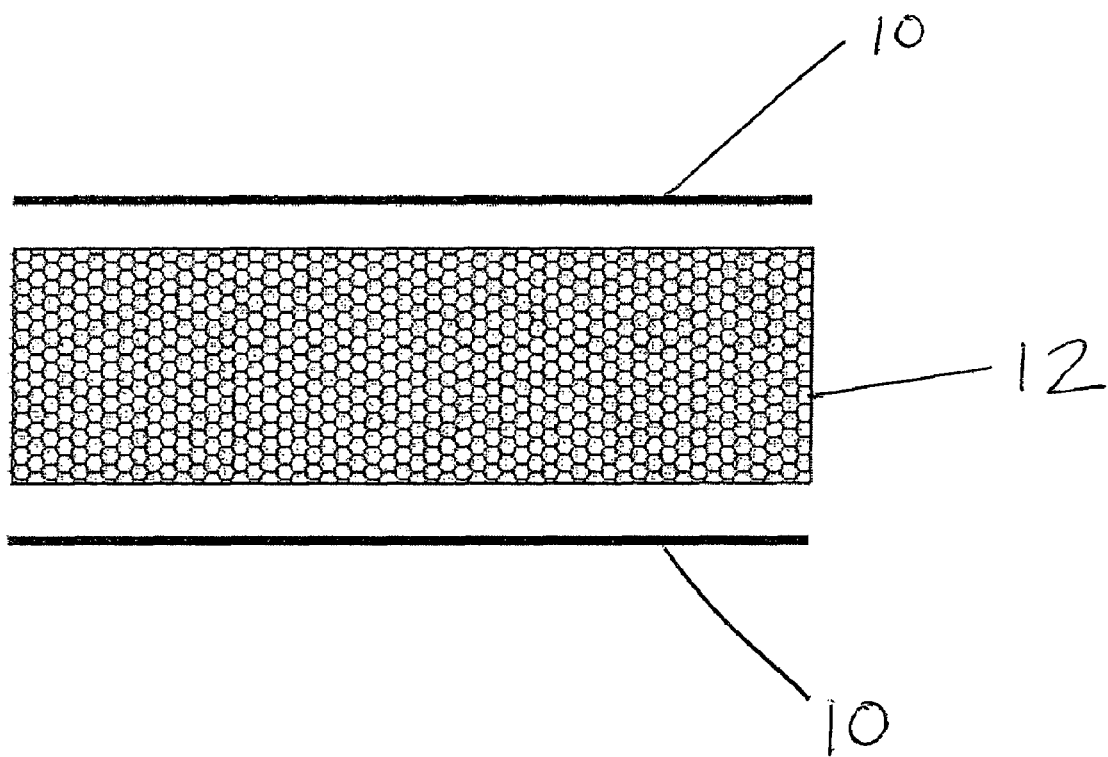
FIG. 1 is cross-section of the low radiation separation member of the present invention.
Figure 6A:
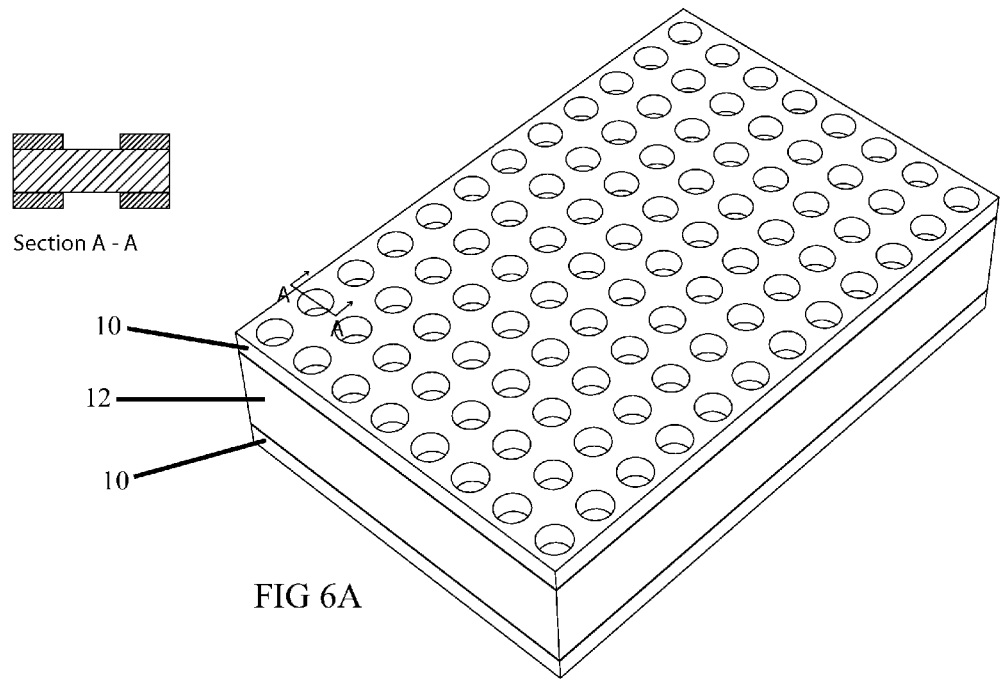
FIGS. 6A and 6B are an elevated view of the low radiation separation member of the present invention.
Figure 6B:
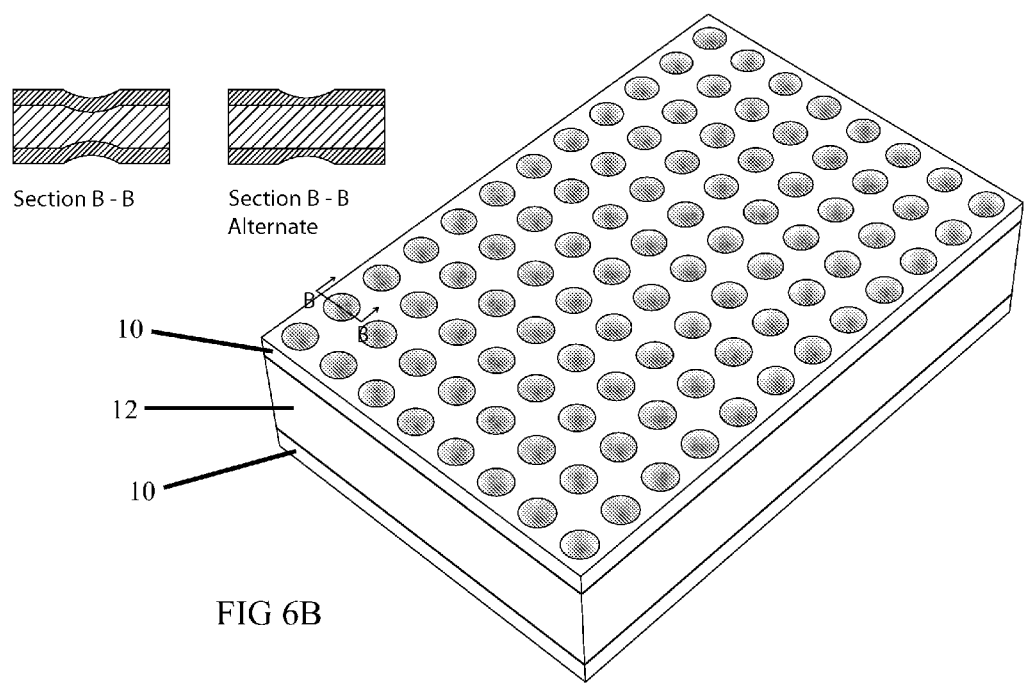

FIG. 1 illustrates the construction of the low radiation absorbing separation member. The core material 12 is sandwiched between two patient contact surfaces 10 creating the low radiation absorbing separation material. The patient contact surfaces 10 can include a fiber reinforced composite material, a polymer sheet or an open weave of filaments. The reinforced composite material can include at least one fiber selected from the group consisting of carbon fiber, aramid fiber, liquid crystal polymer fiber, ultra high molecular weight polyethylene, polypropylene, polyamide, polybutylene-terepthalate, man made fiber, cotton, wood pulp, natural fiber. The polymer sheet can be at least one selected from the group consisting of acrylonitril-butadiene-styrene, polyphenylene oxide, polyethylene, polypropylene, polyester, polyether ether ketone, polyetherimide, polyolefin and phenolic. As shown in FIGS. 6A and 6B, the patient contact surface 10 can be perforated (FIG. 6A) or dimpled (FIG. 6B) such that the surface area of the surface is minimized, thereby reducing the amount of contact between the separation member surface and the patient's skin. The core material can be selected depending upon the desired rigidity and compression characteristics and can include at least one of the group consisting of rigid foam, polyisocyanurate, polyurethane foam, polyisocyanate foam, polymethylmethacrylate foam, polyetherimide foam, polystyrene foam, phenolic foam, aramid honeycomb and paper honeycomb.

Figure 2:
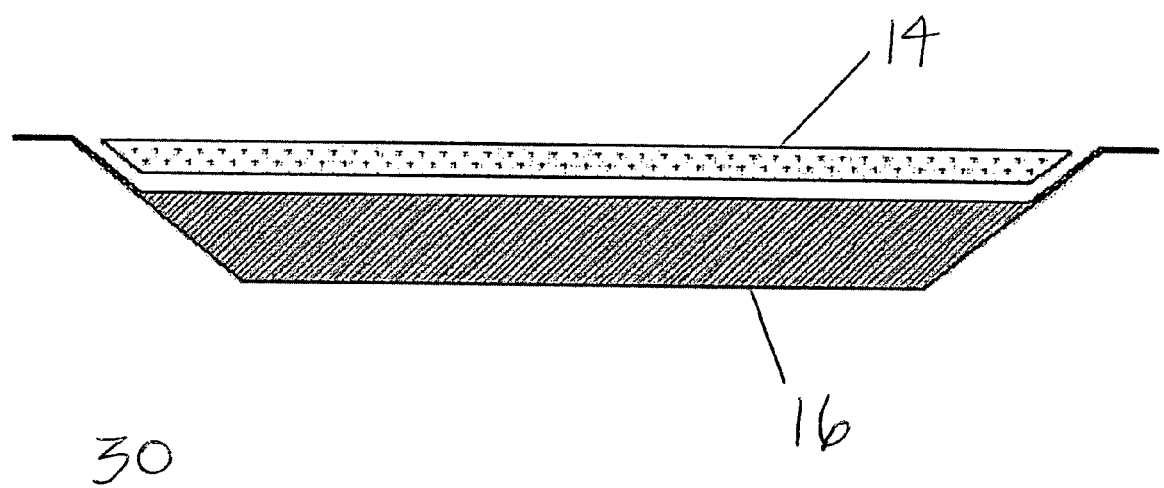
FIG. 2 is a cross-sectional view of one aspect of the present invention.
Figure 3:
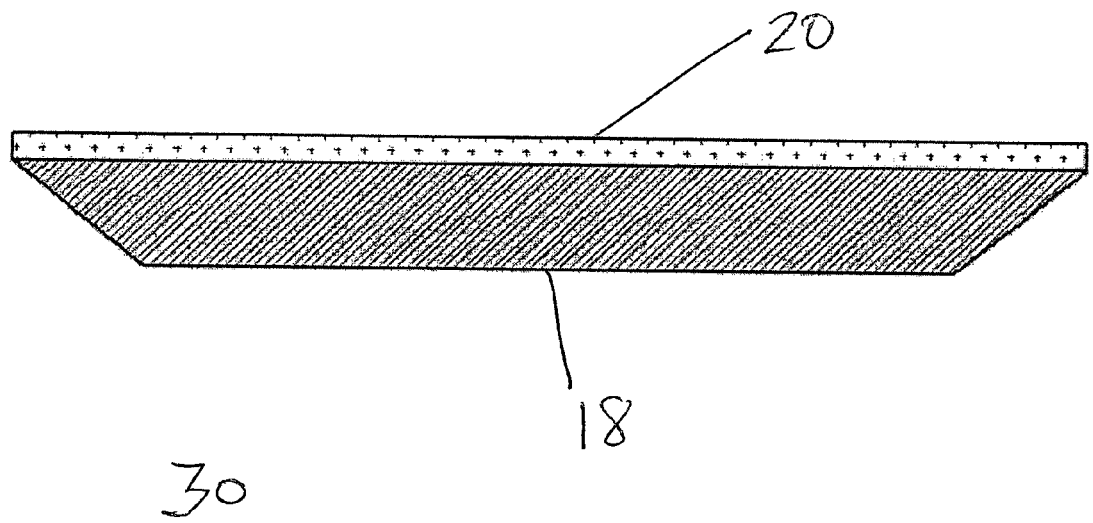
FIG. 3 is a cross-sectional view of another aspect of the present invention.
Figure 4:
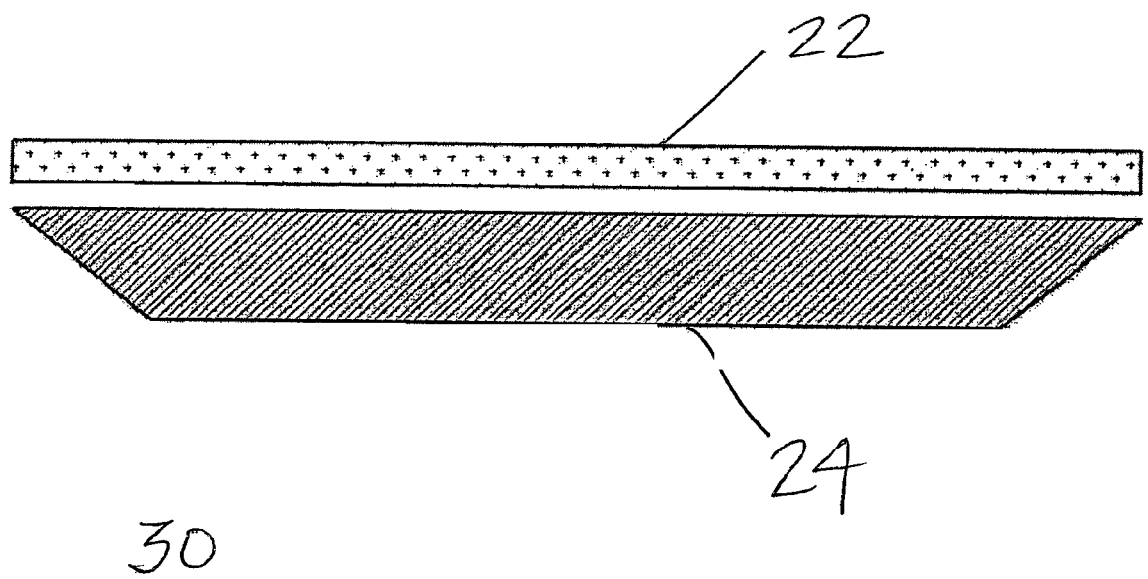
FIG. 4 is a cross-sectional view of another aspect of the present invention.

FIG. 2 illustrates a preferred embodiment of the present invention wherein a patient support top is constructed of a structural element 16 that can receive a low radiation absorbing separation member 14 into the top of the structural element 16. The insertable low radiation absorbing separation member 14 can be a single piece or can be of various shapes and sizes depending upon the patient's treatment area. The separation member is preferably up to about 125.0 mm thick FIG. 3 illustrates another preferred embodiment with the low radiation separation member 20 integrated into the patient support structural member 18. In this embodiment, the patient support top 30 is an integrated single structure that incorporates the low radiation separation member 20 into the overall structure. FIG. 4 illustrates yet another embodiment wherein the low radiation separation member 22 is easily removable from the structural member 24. In these embodiments, the low radiation separation member 22 can be constructed and configured for compatibility with various patient support devices and attachments means. For example, the low radiation separation member 22 can be designed and attached to essentially any indexing means available on the patient support device. Such attachment means can include but are not limited to grooves or notches.

Figure 5:
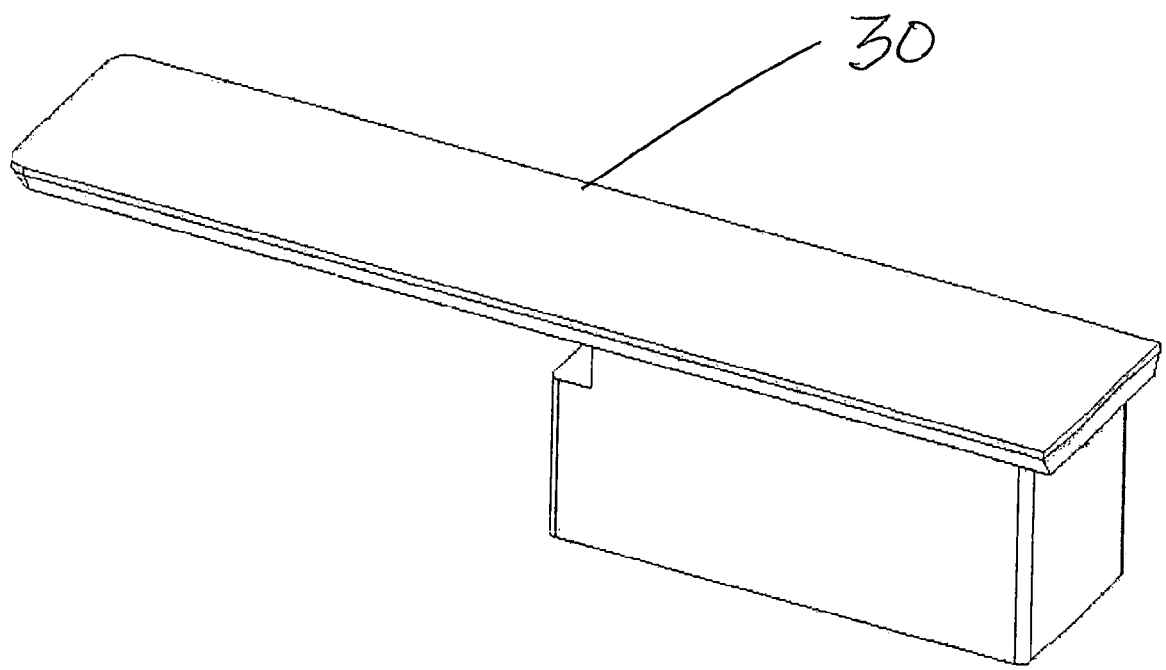
FIG. 5 is a patient support table incorporating one aspect of the present invention.

FIG. 5 shows the integrated patient support table 28 with the low radiation separation member integrated with the structural member.

The present invention can be used and is compatible with conventional patient positioning devices and patient support tables. For example, a breast board, pelvis board or head and neck board, can incorporate the present invention thereby reducing or eliminating radiation skin burn at the specific treatment sites.

The present invention is further defined by the following claims.

I claim:

1. A patient support device comprising a structural element and a multi-layer patient support separation member comprising at least one core structural element with a top surface and a bottom surface, wherein at least one of the surfaces is in contact with a separation layer, and one of the separation layers is a patient contact surface and wherein the multi-layer patient support separation member comprises low radiation absorbing material so that electrons generated during a procedure are diffused thereby reducing electron exposure at the patient contact surface.

2. A multi-layer patient support element of claim 1 wherein the separation member comprises a low radiation absorbing and scattering material that is up to about 125.0 mm thick.

3. The patient support device of claim 1 wherein the multi-layer patient support separation member is removable.

4. The patient support device of claim 1 wherein the structural element is adaptable for receiving a multi-layer patient support separation member insert.

5. A patient support device comprising at least one structural element and a multi-layer patient support separation member of claim 1 and further comprising a low radiation absorbing core of from about 0.25 mm thickness sandwiched between the at least one structural element and the multi-layer patient support separation member.

6. The patient support device of claim 1 wherein the low radiation absorbing material is at least one selected from the group consisting of polyurethane foam, polyisocyanate foam, polymethylmethacrylate foam, polyetherimide foam, polystyrene foam, phenolic foam, aramid honeycomb and paper honeycomb.

7. The patient support device of claim 1 wherein the patient contact surface comprises at least one fiber reinforced composite material.

8. The patient support device of claim 7 wherein the fiber is at least one selected from the group consisting of carbon fiber, aramid fiber, liquid crystal polymer fiber, ultra high molecular weight polyethylene, polypropylene, polyamide, polybutylene terphthalate, man made fiber, cotton, wood pulp, and natural fiber.

9. The patient support device of claim 1 wherein the patient contact surface comprises a polymer sheet.

10. The patient support device of claim 9 wherein the polymer sheet is at least one selected from the group consisting of acrylonitril-butadiene-styrene, polyphenylene oxide, polyethylene, polypropylene, polyester, polyether ether ketone, polyetherimide, polyolefin and phenolic.

11. The patient support device of claim 1 wherein the patient contact surface has perforations.

12. The patient support device of claim 1 wherein the patient contact surface has a dimpled surface.

13. A patient support table comprising a patient support top and at least one multi-layer patient support separation member of claim 1.

14. A patient positioning device comprising a patient support top and at least one multi-layer patient support separation member of claim 1.

15. An indexed patient positioning system comprising a patient support top and at least one positioning device and wherein the at least one positioning device comprises at least one multi-layer patient support separation member of claim 1.

16. The patient support device of claim 1 wherein the patient contact surface comprises an open weave of filaments.

17. The patient support device of claim 1 wherein the separation member comprises a low radiation absorbing and scattering material and is up to about 125.0 mm thick.

* * * * *